United States Patent [19]

Engelfried et al.

[11] 4,029,777
[45] June 14, 1977

[54] 18-METHYL-19-NOR-20-KETOPREGNANES AND PROCESS FOR THE PREPARATION THEREOF

[75] Inventors: Otto Engelfried; Ulrich Kerb; Rudolf Wiechert; Helmut Wachtel; Dieter Palenschat; Reinhard Horowski; Gert Paschelke; Wolfgang Kehr, all of Berlin, Germany

[73] Assignee: Schering Aktiengesellschaft, Berlin and Bergkamen, Germany

[22] Filed: Aug. 5, 1975

[21] Appl. No.: 602,098

[30] Foreign Application Priority Data

Aug. 5, 1974 Germany .......................... 2438020

[52] U.S. Cl. ............................. 424/242; 424/243; 260/397.3; 260/397.4; 260/397.45
[51] Int. Cl.² ..................... C07J 5/00; A61K 31/56
[58] Field of Search ........ 260/397.3, 397.4, 397.45

[56] References Cited

UNITED STATES PATENTS 3,822,297 7/1974 Phillipps et al. .............. 260/397.45
3,822,298 7/1974 Clayton et al. ............... 260/397.45

Primary Examiner—Elbert L. Roberts
Attorney, Agent, or Firm—Millen & White

[57] ABSTRACT

18-Methyl-19-nor-20-keto steroids of the formula

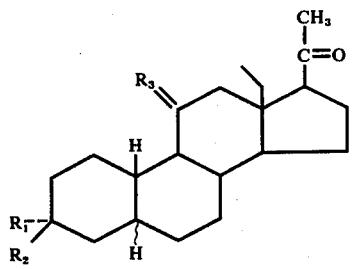

wherein $R_1$ and $R_2$ collectively are an oxygen atom, or each is hydrogen, or one of $R_1$ and $R_2$ is hydrogen and the other is hydroxy, and $R_3$ is a ketonic oxygen atom or two hydrogen atoms, possess CNS-depressant activity, especially anesthetic-narcotic activity.

18 Claims, No Drawings

18-METHYL-19-NOR-20-KETOPREGNANES AND PROCESS FOR THE PREPARATION THEREOF

BACKGROUND OF THE INVENTION

The invention relates to novel 18-methyl steroids. It is known that several steroid compounds, particularly those of the pregnane series, have a CNS-depressant activity, especially anesthetic-narcotic effects, and exert an influence on membrane permeability. J. A. Sutton, Postgrad. Med. J., 48 Suppl. 2 (1972). L. Gyermek et al., J. Med. Chem. 11 (1968) 117.

SUMMARY OF THE INVENTION

In a composition aspect, this invention relates to 18-methyl-19-nor-20-ketopregnanes of the general formula

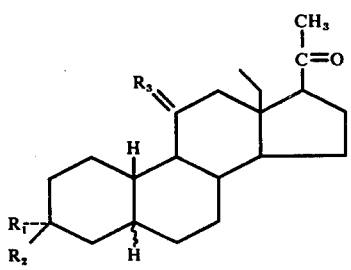

wherein $R_1$ and $R_2$ collectively are an oxygen atom or each is a hydrogen atom, or one of $R_1$ and $R_2$ is a hydrogen atom and the other is hydroxy, and $R_3$ is an oxygen atom or two hydrogen atoms, and the wavy line at the 5-position means the hydrogen atom can be in the α- or β-configuration.

In another composition aspect, this invention relates to novel intermediates in the production thereof.

In a further composition aspect, this invention relates to pharmaceutical compositions comprising a compound of the above formula in admixture with a pharmaceutically acceptable carrier.

In process aspects, this invention relates to processes for the production and use of the novel compounds of this invention.

DETAILED DISCUSSION

Examples of classes of compounds within the scope of this invention are those of the above formula wherein:

a. $R_1$ is hydroxy;
b. $R_2$ is hydroxy;
c. $R_1$ and $R_2$ collectively are a ketonic oxygen atom;
d. the 5-hydrogen atom is α, especially those of (a), (b) and (c);
e. the 5-hydrogen atom is β, especially those of (a), (b) and (c);
f. $R_3$ is an oxygen atom, especially those of (a), (b), (c), (d) and (e);
g. $R_3$ is two hydrogen atoms, especially those of (a), (b), (c), (d) and (e).

The novel 18-methyl-19-nor-20-ketopregnanes possess valuable pharmacological activity. They have, in particular, CNS-depressant activity, especially anesthetic-narcotic activity with a brief induction time and high effectiveness. Upon parenteral administration, they induce anesthesia after a short induction period.

The novel 18-methyl-19-norpregnanes exhibit, compared to the conventional steroids of the pregnane series, a surprisingly brief induction time and high effectiveness. Thus, for example, 3α-hydroxy-18-methyl-19-nor-5β-pregnan-20-one is, after one minute p.i. (after injection), five times more effective than the known sodium 21-hydroxy-5β-pregnane-3,20-dione 21-hemisuccinate.

This superior anesthetic effectiveness was investigated on male NMRI mice weighing 20–25 g. For this purpose, the steroid compounds were suspended in 10% polyhydroxyethylated castor oil and administered intravenously with the addition of 0.9% NaCl solution in a randomized arrangement, wherein the injection volume was 10 ml./kg. of body weight and injection was accomplished within 10 seconds. Directly after injection, the test animals were placed on their backs on a heated plate (35° C.) and the loss of righting reflex was determined. A loss of the righting reflex was present if the test animals did not right themselves within 30 seconds into prone position with all four paws in contact with the ground. The evaluation was done by statistical probit analysis.

The compounds of this invention are especially suitable for the induction of narcosis, wherein anesthesia is maintained after induction of the narcotized condition by an inhalant anesthetic, for example, ether, halothane, laughing gas, etc. For various therapeutic or diagnostic operations, the anesthetic effect of the compounds according to the present invention is even sufficient by itself. The anesthetic effect can be maintained in this instance by repeated or continuous administration, e.g., intravenous infusion. The compounds of this invention, compared to heretofore known steroidal anesthetics, generally lead to only minor undesired side effects.

Anesthetics comprising a compound of this invention are formulated in accordance with the customary pharmaceutical practice with the aid of one or more vehicles, solubilizers or binders. In general, the preparations of the anesthetic compounds of the present invention are administered intravenously, but also in certain cases by intramuscular injection, for example in the case of children.

The range of application encompasses the use of an anesthetic in human as well as veterinary medicine. A dosage of 0.1 – 5 mg./kg. of body weight is generally sufficient for an average person upon intravenous administration. The preferred doses are in the range from 0.2 – 2 mg./kg. The dosage is dependent on the physical condition of the patient and on the degree and duration of the desired narcosis effect. By varying the dose, it is possible to attain periods of narcosis of 10 minutes up to one hour or more. If a longer period of anesthesia is to be maintained, the dose can be repeated, generally the same as the first dose or a smaller dose. For continuous administration, the dose is about 0.05 – 1 mg./kg./minute.

If the anesthetic preparations are administered intramuscularly, higher doses are generally required, usually at least twice as high as in case of intravenous administration.

The novel 18-methyl-19-nor-20-ketopregnanes, especially those compounds wherein $R_1$ and $R_2$ is an oxygen atom, also exhibit anticonvulsive activity. Thus, 18-methyl-19-nor-5β-pregnane-3,20-dione is at least equally as active with respect to convulsion-protective effect in the technical as well as clonic convulsive phase as the conventional sodium phenobarbital, and the novel compound is more compatible.

The anticonvulsive effectiveness was tested on mice of both sexes weighing 20-25 g. The 18-methyl-19-norsteroid to be tested was applied intraperitoneally in a randomized arrangement with 0.9% NaCl solution with the addition of 10% "Cremofor ED" or, in case of sodium phenobarbital, in a 0.9% NaCl solution. The injection volume was 10 ml./kg. of body weight. Per dosage group, 6 animals were employed, and per test compound, 9 doses were utilized. Six animals served as control for the solvent.

The convulsions were triggered by an electroshock applied by way of eye electrodes. The strength of this shock was dimensioned so that nonlethal effects, defined in connection with control animals, were evoked which caused in mice an immediately occurring, generalized tonic convulsion followed by clonic convulsions. Anticonvulsively active substances prevent the occurrence of each or both phases of convulsion.

The electroshock was administered 30 minutes after the intraperitoneal injection of the test substances. The evaluation was conducted after determining the animals showing an effect (absence of tonic or clonic convulsions, respectively, within one minute after shock application) per treatment group by means of statistical probit analysis. For intravenous administration, particularly suitable are aqueous solutions containing one or more surface active vehicles, e.g., polyhydroxyethoxylated castor oil, polyoxyethylenesorbitan monooleate, polyoxyethylenesorbitan monostearate and polyoxyethylenesorbitan monopalmitate. The amount of surface active agent is in the range of 5 – 30% by weight, preferably 5 – 20%.

In a process aspect, this invention relates to processes for the production of 18-methyl-19-nor-20-ketopregnanes of the above-indicated general formula, wherein, in a conventional manner a. a 17β-acetoxy-18-methyl-19-nor-17α-pregnane-3,20-dione of the general formula

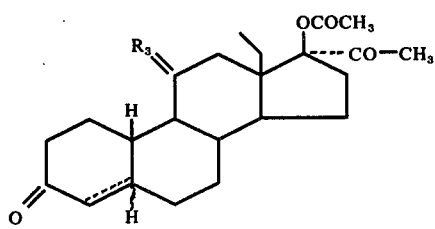

wherein $=$ represents a C—C single or C=C double bond, $R_3$ has the values given above, and a hydrogen atom when present in the 5-position can be in the α- or β-configuration, is treated with an alkali or alkaline earth metal, preferably lithium, in liquid ammonia and any keto group concomitantly reduced is reoxidized to a keto group, or b. an unsaturated 20-keto-18-methyl-19-norpregnane of the general formula

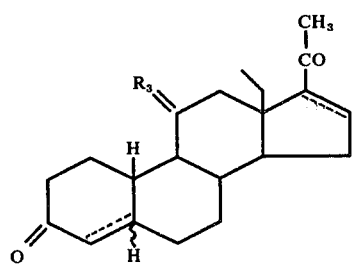

wherein $R_3$ has the values given above and $=$ represents a C—C single or C=C double bond, and the hydrogen atom when present in the 5-position can be in the α- or β-configuration, is hydrogenated and optionally the 3-keto group is selectively reduced to a 3α- or 3β-hydroxy group.

The conversion of the 17β-acetoxy-17α-acetyl steroids to steroids with the normal progesterone side chain is effected, for example, under the conditions of the Birch reaction (J.Am.Chem.Soc. 80 [1958] 6118). For this purpose, an alkali metal, e.g., lithium or sodium, or an alkaline earth metal, e.g., calcium, is introduced into liquid ammonia, and the steroid is added in a suitable solvent. Suitable solvents are cyclic ethers, e.g., tetrahydrofuran or dioxane. However, other inert solvents are also suitable, e.g., 1,2-dimethoxyethane (glyme) or diethylene glycol dimethyl ether (diglyme). A $\Delta^4$-double bond present in the starting material is simultaneously reduced with the formation of preferably the 5α-H-compound.

Since, under the conditions of the Birch reaction, the keto groups are also partially reduced at the same time, it is advantageous, in order to obtain a uniform product, to again oxidize any thus-formed alcohols to the corresponding ketones with a suitable oxidizing agent. A suitable oxidizing medium is, for example, chromium trioxide in aqueous sulfuric acid or acetic acid. Also suitable is an oxidation with dimethyl sulfoxide/$SO_3$ in pyridine in the presence of triethylamine, or with dimethyl sulfoxide/dicyclohexylcarbodiimide (DCC) in pyridine in the presence of trifluoroacetic acid.

For the selective reduction of a keto group in the 3-position in the presence of an 11- and/or 20-keto group, the keto steroid, dissolved in an inert solvent, is either hydrogenated at a temperature below room temperature with a complex metal hydride, such as, for example, lithium aluminum tri-tert.-butoxy-hydride, or with sodium borohydride at room temperature, or directly with hydrogen in the presence of Raney nickel in a lower carboxylic acid, such as, for example, formic acid or acetic acid, under pressure in the range of 30–300 atmospheres gauge. Solvents which are inert with respect to complex metal hydrides are, for example, ethers, e.g., diethyl ether or tetrahydrofuran, dioxane, ethylene glycol dimethyl ether and diethylene glycol dimethyl ether; alcohols, e.g., methanol and ethanol; and pyridine. However, it is also possible to effect the reduction with triphenylphosphine in isopropanol in the presence of iridium tetrachloride.

If the 3-keto steroid additionally contains unsaturated C=C double bonds, the reduction is advantageously carried out directly with hydrogen in the presence of noble metal catalysts in finely divided form, e.g., palladium, on a suitable support, e.g., carbon, strontium carbonate or calcium carbonate. Especially suitable solvents for this purpose are dimethylformamide, triethylamine, pyridine and morpholine. However, as the noble metal catalyst, platinum can also be employed in the form of platinum black. Suitable solvents are, for example, alcohols, e.g., methanol and ethanol; cyclic ethers, e.g., tetrahydrofuran and dioxane; ethyl acetate; and mixtures of these solvents.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

PREPARATIONS 80 g. of d-norgestrel acetate is heated to the boiling point with 24.8 g. of HgSO$_4$, 142 ml. of water, 1,680 ml. of methanol for 2 hours under reflux. Then, the reaction mixture is vacuum-filtered after adding carbon; the filtrate is concentrated to half its volume, diluted with methylene chloride, and the organic phase is washed with water, dried and evaporated. Chromatography on silica gel and recrystallization from hexane/ethyl acetate yields 53 g. of 17β-acetoxy-18-methyl-19-nor-17α-pregn-4-ene-3,20-dione, m.p. 160°–161° C.

27 g. of the aforementioned compound is dissolved in a mixture of 180 ml. of dimethylformamide and 30 ml. of triethylamine and hydrogenated in the presence of 6.8 g. of palladium on calcium carbonate (5%) until 1 millimole of hydrogen has been absorbed per millimole of starting compound. After chromatography on silica gel and repeated fractional crystallization from ethyl acetate/hexane and/or ethyl acetate, 17β-acetoxy-18-methyl-19-nor-5β,17α-pregnane-3,20-dione, m.p. 126.5° – 128.5° C. (ethyl acetate/hexane) and 17β-acetoxy-18-methyl-19-nor-5α,17α-pregnane-3,20-dione, m.p. 225°–226° C. (ethyl acetate) are obtained. The hydrogenation can also be carried out in methanol instead of dimethylformamide and triethylamine.

17-Ethinyl-18-methyl-4,16-estradien-3-one (prepared according to Belgian Patent No. 703,564) is hydrated, as described above, to the 18-methyl-19-nor-4,16-pregnadiene-3,20-dione.

EXAMPLE 1

Under agitation, 1.3 g. of lithium is introduced in incremental portions into 120 ml. of liquid NH$_3$. After 30–40 minutes, 6.5 g. of 17β-acetoxy-18-methyl-19-nor-5β,17α-pregnane-3,20-dione in 80 ml. of tetrahydrofuran is added dropwise to the reaction mixture within one-half hour. After 2 hours, 13 g. of ammonium chloride is added in several portions. The ammonia is allowed to evaporate overnight; the mixture is combined with water, extracted with methylene chloride, the methylene chloride phase is washed neutral with water, dried over sodium sulfate, and evaporated to dryness. The residue is dissolved in 270 ml. of acetone, mixed at 18°–20° C. under agitation with 8.7 ml. of a chromic acid solution (267 mg. of CrO$_3$ in 1 ml. of solution) within 20–30 minutes; after another 30 minutes, the excess oxidizing agent is destroyed by methanol. The reaction mixture is diluted with methylene chloride, the organic phase is washed neutral with water, dried over sodium sulfate, and concentrated by evaporation. After purification by chromatography on silica gel, 3.84 g. of 18-methyl-19-nor-5β-pregnane-3,20-dione is obtained which melts at 117° – 118.5° C. after recrystallization from methylene chloride/hexane.

EXAMPLE 2

3.0 g. of 17β-acetoxy-18-methyl-19-nor-5α,17α-pregnane-3,20-dione is reduced analogously to Example 1 with lithium in liquid NH$_3$ and subsequently oxidized with chromic acid. Chromatography on silica gel yields 1.8 g. of 18-methyl-19-nor-5α-pregnane-3,20-dione which melts at 166° – 166.5° C. after recrystallization from ethyl acetate/hexane.

The same compound is also obtained from 5.0 g. of 17β-acetoxy-18-methyl-19-nor-17α-pregn-4-ene-3,20-dione by analogous reduction and subsequent oxidation, as described above. Yield: 1.7 g., m.p. 158°–161° C.

EXAMPLE 3

5 g. of 18-methyl-19-nor-4,16-pregnadiene-3,20-dione is hydrogenated in 40 ml. of dimethylformamide and 7 ml. of triethylamine in the presence of 1.0 g. of palladium on calcium carbonate until 2 mmol. of hydrogen has been absorbed per mmol. of substance. After chromatography on silica gel and repeated fractional recrystallization from hexane/ethyl acetate, 18-methyl-19-nor-5β-pregnane-3,20-dione, m.p. 116.5° – 118° C., and 18-methyl-19-nor-5α-pregnane-3,20-dione, m.p. 165.5° – 166° C., are obtained. The identity with the compounds described in Example 1 and Example 2, respectively, is confirmed by the mixed melting point and thin-layer chromatography, respectively.

EXAMPLE 4

2.4 g. of 18-methyl-19-nor-5β-pregnane-3,20-dione is hydrogenated in 60 ml. of glacial acetic acid in the presence of Raney nickel at room temperature under increased pressure, with an initial pressure of 150 atmospheres gauge. After fractional crystallization from ethyl acetate and preparative thin-layer chromatography, the products are 1.7 g. of 3β-hydroxy-18-methyl-19-nor-5β-pregnan-20-one, m.p. 143°–144° C., and 50 mg. of 3α-hydroxy-18-methyl-19-nor-5β-pregnan-20-one as an oil which crystallizes after trituration with ether/hexane. After recrystallization from the same solvent mixture, the compound melts at 93.5° – 95° C. The last-mentioned compound is obtained during the reduction of 0.9 g. of 18-methyl-19-nor-5β-pregnane-3,20-dione in pyridine with sodium borohydride as the primary product, with a yield of 0.6 g., in addition to 3β-hydroxy-18-methyl-19-nor-5β-pregnan-20-one.

EXAMPLE 5

1.5 g. of 18-methyl-19-nor-5α-pregnane-3,20-dione is reduced in 18 ml. of pyridine with 0.15 g. of sodium borohydride for 24 hours at room temperature. After preparative layer chromatography, the crude product yields 0.3 g. of 3α-hydroxy-18-methyl-19-nor-5α-pregnan-20-one, m.p. 191.5° – 192.5° C., and 0.8 g. of 3β-hydroxy-18-methyl-19-nor-5α-pregnan-20-one, m.p. 160°–161° C. An analogous result is obtained by the catalytic hydrogenation of the 3,20-diketo compound in methanol in the presence of platinum black.

EXAMPLE 6

Analogously to Example 3, 18-methyl-19-nor-4-pregnene-3,11,20-trione (prepared according to J. Chem. Soc. 1968, 2647 et seq.) is hydrogenated with palladium/hydrogen in dimethylformamide and triethylamine. Chromatography on silica gel and repeated fractional crystallization from hexane/ethyl acetate yield 18-methyl-19-nor-5β-pregnane-3,11,20-trione and 18-methyl-19-nor-5α-pregnane-3,11,20-trione.

EXAMPLE 7

The thus-obtained 18-methyl-19-nor-5β-pregnane-3,11,20-trione is further hydrogenated or reduced analogously to Example 4. Preparative layer chromatography yields 3α-hydroxy-18-methyl-19-nor-5β-pregnane-11,20-dione and 3β-hydroxy-18-methyl-19-nor-5β-pregnane-11,20-dione.

EXAMPLE 8

18-Methyl-19-nor-5α-pregnane-3,11,20-trione is reduced or hydrogenated analogously to Example 5. Preparative layer chromatography yields 3α-hydroxy-18-methyl-19-nor-5α-pregnane-11,20-dione and 3β-hydroxy-18-methyl-19-nor-5α-pregnane-11,20-dione.

EXAMPLE 9

4.21 g. of 3β-hydroxy-18-methyl-19-nor-5α-pregnan-20-one is dissolved in 80 ml. of tetrahydrofuran. After adding 7.3 g. of triphenylphosphine and 1.0 ml. of formic acid (98–100% strength), a solution of 4.11 ml. of the diethyl ester of azodicarboxylic acid in 26 ml. of tetrahydrofuran is added gradually dropwise to the reaction mixture under agitation at room temperature. After 2 hours, the reaction mixture is stirred into ice water, and the thus-separated compound is taken up in methylene chloride. The methylene chloride solution is washed with water, dried, and evaporated. Chromatography on silica gel yields 3.5 g. of 3α-formyloxy-18-methyl-19-nor-5α-pregnan-20-one which melts at 130° – 131.5° C. after recrystallization from methylene chloride/hexane. For the hydrolysis of the ester, 1.6 g. of the formyloxy compound is dissolved in 16 ml. of methylene chloride and combined under agitation at room temperature with a solution of 0.35 g. of potassium hydroxide in 16 ml. of methanol. After 30 minutes, the reaction is so complete that no starting material can be detected any more in the thin-layer chromatogram. The reaction mixture is acidified with acetic acid, diluted with water, extracted with methylene chloride; the organic phase is washed with water, dried, and evaporated. Recrystallization from ethyl acetate yields 1.2 g. of 3α-hydroxy-18-methyl-19-nor-5α-pregnan-20-one, m.p. 189° – 190.5° C. The identity of this product with the 3α-hydroxy compound described in Example 5 is confirmed by the mixed melting point and thin-layer comparison.

EXAMPLE 10

8 grams of finely ground 3α-hydroxy-18-methyl-19-nor-5β-pregnan-20-one is dissolved in 200 grams of polyhydroxyethoxylated castor oil at 50° C and the solution is completed to one liter with a 0.25% aqueous solution of sodium chloride. The solution is filtered by a membrane filter to an aseptic condition and filled into ampoules for intravenous administration.

EXAMPLE 11

2.5 grams of 3α-hydroxy-18-methyl-19-nor-5β-pregnan-20-one is dissolved in 200 grams of polyoxyethylen-sorbitanmonooleate at 60° C, completed to one liter with a 0.25% solution of sodium chloride in water, filtered and filled into ampoules under aseptic conditions.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

Wat is claimed is:

1. An 18-methyl-19-nor-20 ketopregnane of the formula

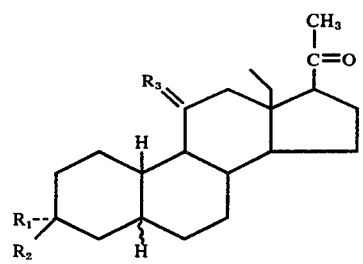

wherein $R_1$ is a hydrogen atom and $R_2$ is hydroxy, and $R_3$ is an oxygen atom or two hydrogen atoms.

2. 3β-Hydroxy-18-methyl-19-nor-5β-pregnan-20-one, a compound of claim 1.
3. 3α-Hydroxy-18-methyl-19-nor-5β-pregnan-20-one.
4. 3β-Hydroxy-18-methyl-19-nor-5α-pregnan-20-one, a compound of claim 1.
5. 3β-Hydroxy-18-methyl-19-nor-5β-pregnane-11,20-dione, a compound of claim 1.
6. 3α-Hydroxy-18-methyl-19-nor 5α-pregnane-11,20-dione.
7. 3β-Hydroxy-18-methyl-19-nor-5α-pregnane-11,20-dione, a compound of claim 1.
8. An 18-Methyl-19-nor-20-ketopregnane of the formula

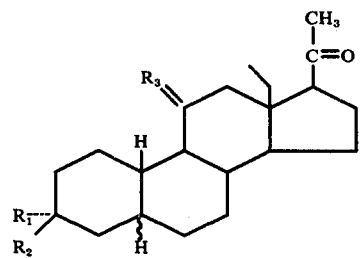

wherein $R_1$ and $R_2$ collectively are an oxygen atom and $R_3$ is an oxygen atom or two hydrogen atoms.

9. A compound of claim 8 wherein $R_3$ is an oxygen atom.
10. 18-Methyl-19-nor-5β-pregnane-3,20-dione, a compound of claim 8.
11. 18-Methyl-19-nor-5α-pregnane-3,20-dione, a compound of claim 8.
12. 18-Methyl-19-nor-5β-pregnane-3,11,20-trione, a compound of claim 8.
13. A sterile, injectable pharmaceutical composition comprising an anesthetic amount per unit dosage of a compound of claim 1 in admixture with a pharmaceutically acceptable carrier.
14. A method of inducing anesthesia in a mammal which comprises the parenteral administration of an amount of a compound of claim 1 effective to render the patient unconscious.
15. A sterile, injectable pharmaceutical composition comprising an anesthetic amount per unit dosage of a compound of claim 6 in admixture with a pharmaceutically acceptable carrier.
16. A method of inducing anesthesia in mammals which comprises the parenteral administration of an amount of a compound of claim 6 effective to render the patient unconscious.

17. A sterile, injectable pharmaceutical composition comprising an anesthetic amount per unit dosage of a compound of claim 8 in admixture with a pharmaceutically acceptable carrier.

18. A method of inducing anesthesia in mammals which comprises the patenteral administration of an amount of a compound of claim 8 effective to render the patient unconscious.

* * * * *